(12) United States Patent
Phillips et al.

(10) Patent No.: US 7,758,502 B2
(45) Date of Patent: Jul. 20, 2010

(54) SLIDE AND SNAP CLAMP

(75) Inventors: Burns Phillips, Nashville, TN (US); Larry Griffith, Lakeville, MN (US)

(73) Assignee: Boss Instruments, Ltd., Earlysville, VA (US)

( * ) Notice: Subject to any disclaimer, the term of this patent is extended or adjusted under 35 U.S.C. 154(b) by 566 days.

(21) Appl. No.: 10/819,830

(22) Filed: Apr. 7, 2004

(65) Prior Publication Data
US 2005/0224668 A1 Oct. 13, 2005

(51) Int. Cl.
*A61B 1/32* (2006.01)
(52) U.S. Cl. .......... 600/234; 248/68.1; 248/229.2
(58) Field of Classification Search .......... 248/229.11, 248/229.13, 229.21, 229.23, 231.31, 231.51, 248/316.2, 316.5, 227.4, 541, 68.1; 403/391, 403/389, DIG. 8, DIG. 9, 385, 396, 64; 24/514, 24/535; 600/230, 234, 201, 227
See application file for complete search history.

(56) References Cited

U.S. PATENT DOCUMENTS

| 1,839,726 | A | | 1/1932 | Arnold | |
|---|---|---|---|---|---|
| 2,452,406 | A | * | 10/1948 | Volkery et al. | 403/391 |
| 4,497,092 | A | | 2/1985 | Hoshino | |
| 4,949,707 | A | * | 8/1990 | LeVahn et al. | 600/234 |
| 5,172,877 | A | * | 12/1992 | Hattori et al. | 248/68.1 |
| 5,897,087 | A | | 4/1999 | Farley | |
| 6,017,008 | A | | 1/2000 | Farley | |
| 6,033,363 | A | * | 3/2000 | Farley et al. | 600/234 |
| 6,277,069 | B1 | * | 8/2001 | Gray | 600/234 |
| 6,802,633 | B1 | * | 10/2004 | VandenBossche | 362/477 |

FOREIGN PATENT DOCUMENTS

EP 0972491 A1 1/2000

OTHER PUBLICATIONS

International Search Report for related application No. PCT/US2006/019061, mailed Oct. 6, 2006.

* cited by examiner

*Primary Examiner*—Gwendolyn Baxter
(74) *Attorney, Agent, or Firm*—McDermott Will & Emery LLP

(57) ABSTRACT

A slide and snap clamp provides a first clamping member with first and second clamping sections. The first clamping section is located adjacent the hinge while the second clamping section and the hinge on opposite sides of the first clamping section. An actuator is used to transition the first clamping member from an unlocked or locked configuration with a rail in one of the first and second clamping sections. The first and second clamping sections are configured to receive the rail A at a predetermined cross sectional perimeter in either of the first and second clamping sections. The operator selects which of the two clamping sections be utilized the actuator can be transitioned and locked position thereby securing the rail to the first clamping member.

15 Claims, 2 Drawing Sheets

SLIDE AND SNAP CLAMP

BACKGROUND OF THE INVENTION

1. Field of the Invention

This invention relates to a retractor clamp, and more particularly to a clamp configured to attached to a frame while receiving a second shaft at a second clamping location such as a shaft connected to a retractor.

2. Description of Related Art

Over the years, numerous retractor clamps have been provided including U.S. Pat. Nos. 1,839,726, 4,497,092, 4,949,707, 5,897,087, 6,017,008, and 6,277,069.

U.S. Pat. No. 4,949,707 shows one style clamp which has two clamping sections 40,42 which are rotatably positionable relative to another. Rotation of a bolt 46 locks the clamping aperture 62,70 by reducing the perimeter of the clamping aperture when the handle is rotated in a locking direction. The clamping aperture is located intermediate a hinge and the bolt 46.

U.S. Pat. No. 6,277,069 works in a similar fashion except that the actuator or bolt is closer to the hinge than the clamping aperture in this configuration. In this design, a bar can be snapped into position while a bar must be slid into position on clamping sections as shown in U.S. Pat. No. 4,949,707. It is important to observe that in U.S. Pat. No. 6,277,069 that the bore 39 adjacent to the hinge 33 does not provide a clamping aperture. Since it is much smaller than the rail cross-section for which the clamp works.

Accordingly, there is believed to be a need to provide a single clamping member with the capability of providing two clamping apertures: one, a snap-on type; the other a slide-in type.

SUMMARY OF THE INVENTION

Accordingly, it is an object of the invention that a clamping member having a first and a second clamping section.

It is another object of the present invention to provide a clamping member having a first clamping section located adjacent a hinge member and a second clamping section. The first clamping member is located intermediate the second clamping section and the hinge member.

It is yet another object of the present invention to provide a clamping member having an actuator intermediate a first clamping second and a second clamping section wherein the first and second clamping sections are adapted to receive a similarly sized rail.

Accordingly, a slide and snap clamp provides an actuator which connects two clamping members together. The first clamping member has two clamping sections one of which is disposed on either side the actuator. A first clamping section is located proximate to a hinge and a second clamping section is located opposite the actuator from the first clamping section. The first and second clamping sections are both configured to receive a rail of a predetermined circumference. A user may select which of the first and second clamping sections to receive the rail.

The second clamping member preferably has a single clamping section which may receive a second rail, stem or other appropriate extension member therethrough. The first and second clamping members are rotatably positionable relative to one another. The actuator locks the first and second clamping members as well as sets the angular position of the first clamping member relative to the second clamping member.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
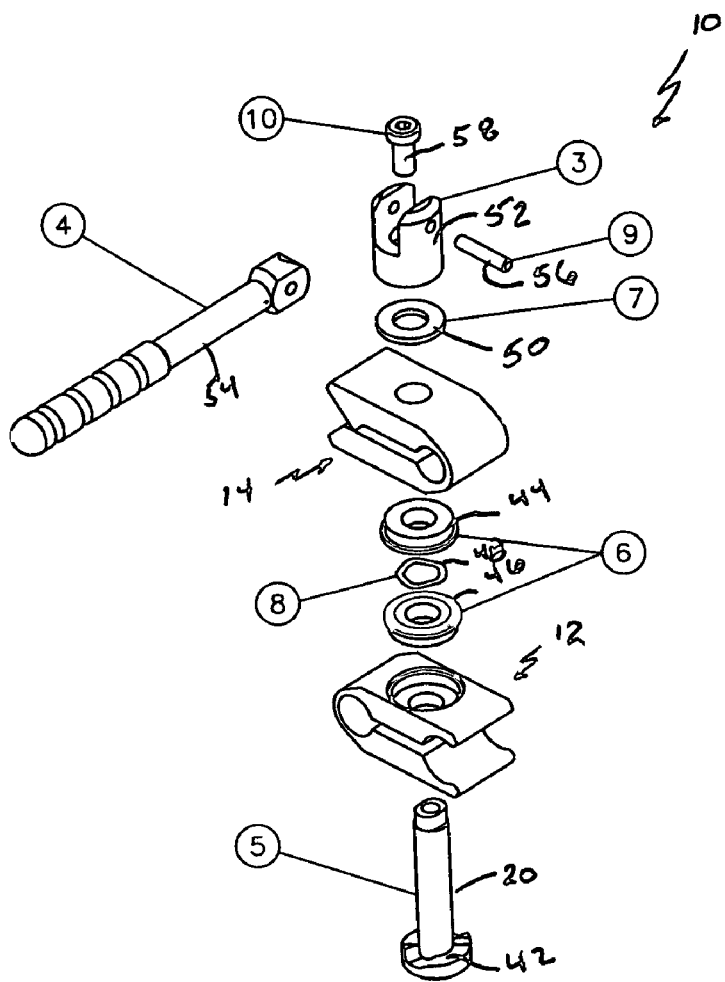
FIG. 1 is an exploded view of the presently preferred embodiment of a clamp constructed in accordance with the presently preferably embodiment of the present invention.
Figure 2:
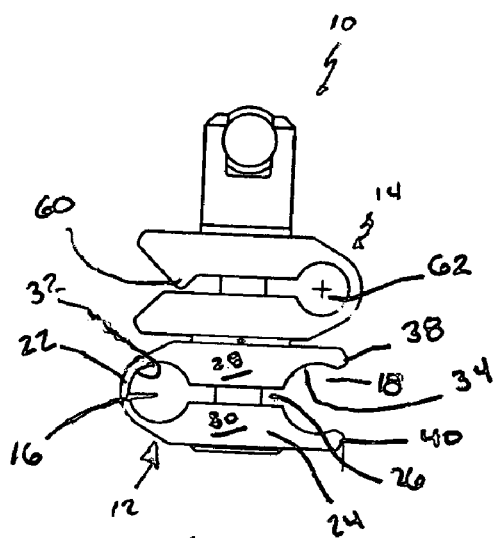
FIG. 2 is a front plan view of the clamp of FIG. 1.
Figure 3:
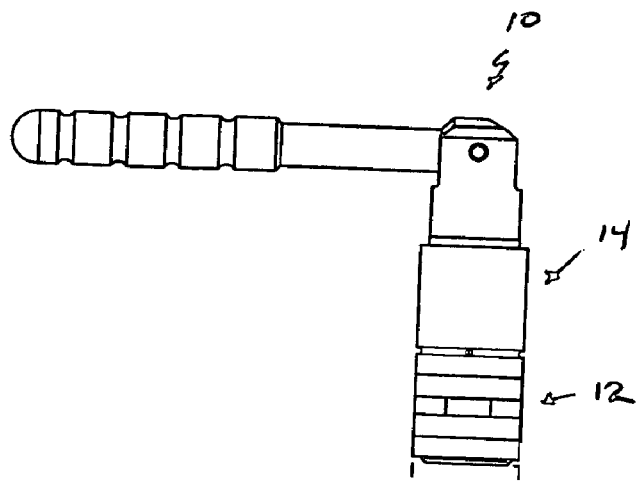
FIG. 3 is a side plan view of the clamp in FIG. 1.

FIGS. 1-6 show a clamp 10. The clamp is comprised of a first clamping member 12, and in the preferred embodiment, a second clamping member 14. The first clamping member 12 has first and second clamping sections 16,18. The first and second clamping sections 16,18 are preferably located opposite one another from a portion of the actuator 20 as will be described in further detail below. The first clamping section 16 is preferably located adjacent to hinge 22 as shown in FIG. 2. The first clamping member 12 is preferably constructed out of a unitary body 24 with the clamping sections 16,18 formed therein. Furthermore, a slot 26 connects the first and second clamping sections 16,18. The first clamping member 12 has a top 28 and a bottom 30 spaced by the slot 26 in the preferred embodiment. As the top and bottom 28,30 are pushed towards one another by operation of the actuator 20 as will be explained in further detail below, the distance therebetween represented by slot 26 is reduced. As this distance is reduced, a perimeter 32 of the first clamping section 16 as well as a perimeter 34 of the second clamping section 18 is reduced. As the top and bottom 28,30 are pushed towards one another, the hinge 22 yields and/or allows a pivoting of the top 28 relative to the bottom 30.

The clamp 10 has an open configuration as shown in FIG. 2. In this configuration, a rail such as the rail 36 shown in FIGS. 4 and 5 has a slightly smaller perimeter than the first and second perimeters 32,34. Accordingly, the rail 36 may be slid into either the first or second clamping sections 16,18. Furthermore, in the second clamping section 18, the construction of the second clamping section 18 with the legs 38,40 spaced from one another by a gap, allows for the rail 36 to be snapped into the second clamping location 18 as will be explained in further detail below. Snapping into position is not an option for the first clamping section 16 in the preferred embodiment (i.e., hinge 22 would prevent the insertion of a rail 36 in this manner).

Figure 4:
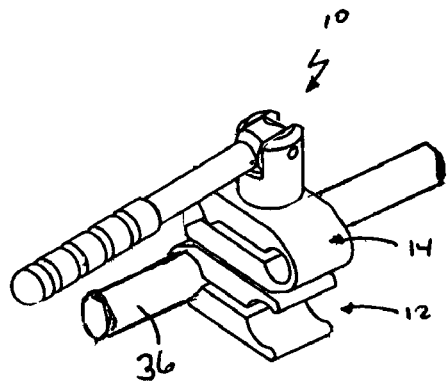
FIG. 4 shows the clamp connected to a rail at a first clamping section.

The rail 36 shown in FIG. 4 has a perimeter which cooperates with the first and second perimeters 32,34. That is to say that the same rail 36 can be inserted into either of the first and second clamping sections 16,18. This is not possible in the prior art since the bore located adjacent to the hinge such as in U.S. Pat. No. 6,277,069 has a much smaller perimeter than the clamping section. There is no way to modify this structure to receive a particular rail in either the bore 39 or the clamping aperture 35.

FIG. 1 shows the remainder of the parts of the preferred embodiment of the clamp 10. The actuator 20 has a cam surface 42. Threads could also be utilized or any other actuator style could also be utilized. Serrated washers 44,46 oppose one another and are biased away from one another by spring 48. Washer 50 is located intermediate the second clamping member 14 and head 52 which receives handle 54. The handle 54 connects to the head 52 pin 56. A bolt 58 may be useful in connecting the head 52 to the actuator 20 which is illustrated as a draw bolt. Rotation of the handle 54 rotates the head 52 which is connected to the draw bolt 20. This rotates the cam surface 42 thereby overcoming the bias of the spring 48 to not only lock the angular position of the first and second clamping members 12,14 but to also transition the clamping members 12,14 from an open configuration as shown in FIG. 1 and FIG. 2 to the closed configuration as shown in FIGS. 4 and 5.

The second clamping member 14 has a stop 60 so that the first clamping member 12 can be appropriately positioned even if there is no rail stem or other extension extending through clamping aperture 62 in the second clamping member 14.

Figure 6:
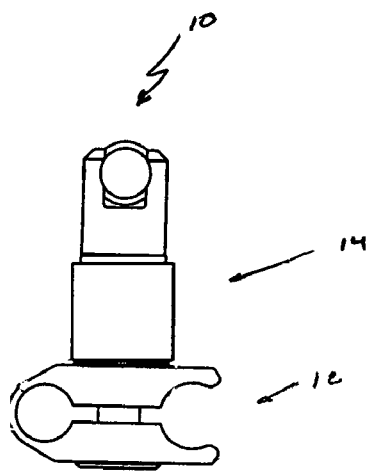
FIG. 6 shows the clamp with the first clamping member twisted relative to the second clamping member.

FIG. 6 shows that the first clamping member 14 is rotatable relative to the second clamping member 14.

Figure 5:
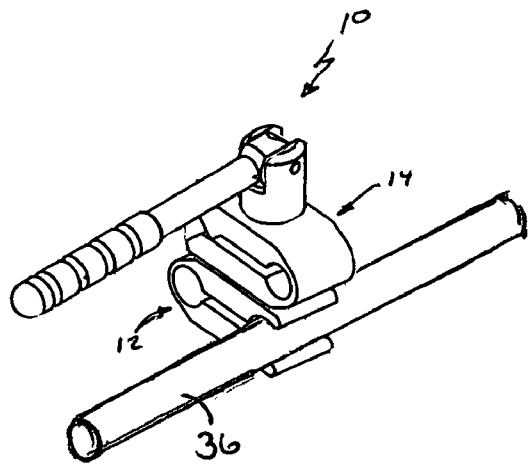
FIG. 5 shows the clamp connected to a rail at the second clamping location.

FIGS. 4 and 5 show a single rail 36 preferably having a constant cross-section and more preferably having a circular cross-section is retained in the first clamping section 16 shown in FIG. 4, and then in the second clamping section 18 shown in FIG. 5. This is the same rail 36 shown in both FIGS. 4 and 5. Accordingly, in order for this to occur, the perimeters 32,34 or circumferences 32,34 are slightly larger than the circumference of the rail 36 when the clamp 10 is in an unlocked configuration. This allows the rail 36 to be slid into the first clamping section 16. The rail 36 could also be slid into the second clamping section 18 but is more preferably snapped into the second clamping section by placing the rail 36 against the legs 38,40 than pushing towards the hinge 22. This displaces the legs 38,40 from one another thereby temporarily increasing the distance of the separation of the slot 26 relative to the top and bottom 28,30 of the body 24. As the diameter of the rail 36 passes through the legs 38,40, the width of the rail decreases and the legs 38,40 come back towards one another. When the clamp is unlocked, the rail 36 can preferably be slid through the clamping section 18 as well as the first clamping section 16. When the clamp is transitioned to the locked configuration as explained above, the top and bottom 28,30 are moved toward one another by operation of the actuator 20 and the perimeters 32,34 decrease until the perimeters correspond to the perimeter of the rail 36 and the locking engagement is then formed by continuing to apply a closing force.

The marked difference between this clamp 10 and the prior art is the ability for a single clamping member 12 to receive a similarly configured rail 36 in either of a first and second clamping sections 16,18 of a clamping member 12.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A clamp comprising:
   a first clamping member having a top and bottom connected at a hinge;
   a first clamping section adjacent the hinge intermediate the top and bottom, the first clamping section having a cross-sectional perimeter;
   a second clamping section intermediate the top and bottom, the second clamping section having a cross-sectional perimeter sized substantially the same as the cross-sectional perimeter of the first clamping section;
   a slot connecting the first clamping section to the second clamping section;
   said first and second clamping sections each having an unlocked configuration and a locked configuration, wherein the first clamping section is connected to the second clamping section in the locked configuration and in the unlocked configuration, wherein when in said unlocked configuration a rail of a predetermined cross section perimeter is positionable in the first and second clamping sections, and wherein when in the locked configuration, the rail is secured to a selected one of the first and second clamping sections at the predetermined cross section perimeter;
   an actuator having a cam surface operably connected to the first clamp member wherein operation of the actuator adjusts the cam surface to transition both the first clamping section and the second clamping section from the unlocked to the locked configuration, wherein the first clamping member is connected to a second clamping member in the locked and unlocked configuration, and wherein the first clamping member is adapted to allow the rail to be radially inserted and removed from the second clamping section of the first clamping member in the unlocked configuration;
   said second clamping section of the first clamping member having displaceable legs extending from the top and bottom of the first clamping member and defining a gap therebetween having a gap distance between the first and second legs, wherein the gap distance increases in size when the rail is radially forced against the legs to displace the legs during insertion and removal of the rail, and wherein when the rail is in the clamping section the legs return toward one another after the rail is removed from the second clamping section and when the rail is positioned in the second clamping section; and
   the second clamping member having a first clamping section operable from an unlocked to a locked configuration, and wherein operation of the actuator transitions the second clamping member from the unlocked to the locked configuration.

2. The clamp of claim 1 wherein the actuator extends through at least a portion of the first and second clamping members, and the first clamping member is rotationably positionable relative to the second clamping member about the actuator.

3. The clamp of claim 1 wherein the first clamp member is constructed of a unitary body comprising the top, bottom and hinge and the top and bottom are spaced by the slot and the first and second clamping sections.

4. The clamp of claim 1 wherein the rail has a circular cross section perimeter.

5. A clamp comprising:
   a first clamping member having a top and bottom connected at a hinge, and a first and second clamping section intermediate the top and bottom;
   said first and second clamping sections each having an unlocked configuration and a locked configuration, wherein the first clamping section is connected to the second clamping section in the locked configuration and in the unlocked configuration, wherein when in said unlocked configuration the rail is movable through the first and second clamping sections, and wherein when in the locked configuration, the rail is secured to a selected one of the first and second clamping sections at the predetermined cross section perimeter;

a second clamping member having a top and bottom connected at a hinge, and a clamping section intermediate the top and bottom;

an actuator operably connected to the first and second clamping members wherein operation of the actuator transitions the first and second clamping members from the unlocked to the locked configuration, wherein the first clamping member is connected to the second clamping member in the locked and unlocked configuration, and wherein the first clamping member is adapted to allow the rail to be radially inserted and removed from the second clamping section of the first clamping member in the unlocked configuration; and, said second clamping section of the first clamping member having displaceable legs extending from the top and bottom of the first clamping member and defining a gap therebetween having a gap distance between the first and second legs, wherein the gap distance increases in size when the rail is radially forced against the legs to displace the legs during insertion and removal of the rail, and wherein when the rail is in the clamping section the legs return toward one another after the rail is removed from the second clamping section and when the rail is positioned in the second clamping section.

6. The clamp of claim 5 wherein operation of the actuator moves the top toward the bottom of the first clamping member.

7. The clamp of claim 6 wherein the first clamping member further comprises a slot extending from the first clamping section to the second clamping section and movement from the unlocked to the locked configuration shortens a width of the slot.

8. The clamp of claim 5 wherein the first and second clamping sections have perimeters which substantially correspond in shape to a predetermined cross section perimeter of a rail.

9. The clamp of claim 5 wherein the actuator has a cam surface operably connected to the first clamp member, and wherein operation of the actuator adjusts the cam surface to transition both the first clamping section and the second clamping section of the first clamp member from the unlocked to the locked configuration.

10. The clamp of claim 5 wherein the first clamping member is of unitary construction.

11. The clamp of claim 5 wherein the actuator extends through the top of the first clamping member and at least partially through the bottom.

12. The clamp of claim 11 wherein the actuator is located intermediate the first and second clamping sections.

13. The clamp of claim 5, wherein the second clamping member has a stop protruding from the top member to preclude said top and the bottom members from being moved toward one another past a predetermined distance such that the top and bottom members are spaced a distance apart from one another in the locked configuration.

14. A clamp comprising:

a first clamping member having a top and bottom connected at a hinge;

a first clamping section between the top and bottom, the first clamping section having an unlocked configuration and a locked configuration;

an aperture in the top and bottom of the first clamping member;

an actuator having a shaft and a cam surface, the shaft of the actuator extending through the aperture in the top and bottom to rotatably position the actuator within the first clamping member, and the cam surface of the actuator operably engaging the first clamping member to transition the first clamping section from the unlocked configuration to the locked configuration by rotation of the actuator shaft;

a second clamping member, the actuator extending through the second clamping member to secure the second clamping member thereto, the second clamping member having a top and bottom connected at a hinge, and a closed clamping section partially defined by the hinge intermediate the top and bottom; and said second clamping member having a stop protruding from the top member to preclude said top and the bottom members from being moved toward one another past a predetermined distance such that the top and bottom members are spaced a distance apart from one another in the locked configuration.

15. The clamp of claim 14, wherein the first and second clamping sections having generally the same cross-sectional perimeter.

* * * * *